United States Patent [19]
Yoshino et al.

[11] 4,217,285
[45] Aug. 12, 1980

[54] PROCESS FOR THE PREPARATION OF DL-α-TOCOPHEROL OF HIGH PURITY

[75] Inventors: Youziro Yoshino; Kazuko Kondo, both of Kawagoe, Japan

[73] Assignee: Nisshin Flour Milling Co., Ltd., Tokyo, Japan

[21] Appl. No.: 11,882

[22] Filed: Feb. 13, 1979

Related U.S. Application Data

[63] Continuation of Ser. No. 837,640, Sep. 28, 1977, abandoned.

[30] Foreign Application Priority Data

Sep. 29, 1976 [JP] Japan ................................. 51-115965

[51] Int. Cl.² .......................................... C07D 311/72
[52] U.S. Cl. .................................................. 260/345.5
[58] Field of Search ...................................... 260/345.5

[56] References Cited

U.S. PATENT DOCUMENTS

| 2,411,969 | 12/1946 | Karrer et al. | 260/345.5 |
| 3,444,213 | 5/1969 | Nelan | 260/345.5 |
| 3,459,773 | 8/1969 | Moroe et al. | 260/345.5 |

Primary Examiner—Nicky Chan
Attorney, Agent, or Firm—Haseltine, Lake & Waters

[57] ABSTRACT

A process for preparing high purity dl-α-tocopherol by condensing trimethylhydroquinone and a phytol in the presence of zinc chloride, a mineral acid and, either silica-alumina or silica gel, or a combination of silica-alumina and silica gel, is described.

1 Claim, No Drawings

PROCESS FOR THE PREPARATION OF DL-α-TOCOPHEROL OF HIGH PURITY

This is a Rule 60 Continuation of U.S. Patent Application Ser. No. 837,640, filed Sept. 28, 1977, now abandoned.

This invention relates to a process for the preparation of dl-α-tocopherol, and more particularly, it relates to a process for the preparation of dl-α-tocopherol of high purity by reacting trimethyl hydroquinone with a phytol in the presence of silica-alumina and/or silica gel, zinc chloride and protonic acid.

For the preparation of dl-α-tocopherol, there has been heretofore known the condensation in the presence of a protonic acid catalyst such as p-toluenesulfonic acid in an organic solvent, a Lewis acid catalyst such as zinc chloride or a solid acid catalyst such as silica-alumina. In the preparation of dl-α-tocopherol according to such process, however, formation of by-product arises and such by-product has been impossible to be removed even by repeated purification procedures. Consequently, it has been almost impossible according to the known process to commercially obtain a product with the purity of more than 96% as defined in the rule of U.S. National Formula 14 edition with regard to dl-α-tocopherol acetate even by repeating highly vacuum distillation.

As a result of extensive investigations for a process for the preparation of dl-α-tocopherol of high purity, we have found the process for obtaining dl-α-tocopherol of high purity which comprises as mentioned hereinbefore the condensation of trimethyl hydroquinone and a phytol in the presence of silica-alumina and/or silica gel, zinc chloride and a protonic acid.

As a phytol, one of the starting materials of this invention, not only phytol itself but also its reactive derivatives such as halide e.g. phytyl chloride and phytyl bromide and alkyl esters e.g. phytyl acetate and phytyl propionate can be used. As a protonic acid usable in the process of this invention, hydrochloric acid, sulfuric acid, phosphoric acid or p-toluenesulfonic acid is included and hydrochloric acid is particularly preferable.

As a reaction solvent, a less polar solvent [having a dielectric constant of less than 3 (20°)], for example, an aliphatic hydrocarbon such as n-hexane, isooctane, petroleum ether, etc.; an aromatic hydrocarbon such as benzene, toluene, xylene, etc.; an alicyclic compound such as cyclohexane, tetraline, etc.; a hydrocarbon halide such as carbon tetrachloride, etc.; or a cyclic ether such as dioxane is used with particularly preferable result.

If necessary, each of silica-alumina, silica gel and zinc chloride which are used in the practice of the process of this invention may be fired. Silica-alumina and/or silica gel may preferably be used in the approximately same amount as trimethyl hydroquinone and zinc chloride may be used in a catalytic amount. Further, a protonic acid is preferably added in an amount of about 0.5–5.0% of phytol. The reaction condition is variable due to the combination of the starting materials, solvent and catalyst used and, in general, the reaction temperature of 50°–120° C. and the reaction time of 1–5 hours are satisfactory without any intention of limiting the invention to these ranges. The reaction product can be purified, for example, by washing the reaction mixture with water and an aqueous alkali solution, dehydrating the solvent and effecting, if necessary, acetylation and thereafter distillating under high vacuum.

According to the process of this invention, highly pure dl-α-tocopherol acetate can be obtained by subjecting crude dl-α-tocopherol acetate to only once vacuum distillation. Thus, the process of this invention can be said to be extremely convenient in commercial sense.

Superiority of the present process to the prior known process will be shown by the following comparison: The condensation took place using 25.0 g of isophytol, 13.5 g of trimethyl hydroquinone, 13.5 g of silica-alumina or silica gel, 6.0 g of zinc chloride and 0.5 g of protonic acid. After acetylation of the resulting dl-α-tocopherol in a conventional manner, the fraction of 165°–175° C./8×10$^{-3}$ mmHg was recovered through vacuum distillation. Determination of purity was carried out by gas chromatography using n-dotriacontane as the inner standard. The results obtained are shown in the Table 1.

Table 1

| Catalyst used | Reaction Condition | | | dl-α-tocopherol | | dl-α-tocopherol acetate | | |
|---|---|---|---|---|---|---|---|---|
| | Reaction solvent | Reaction temperature | Reaction time (hr) | Yield (%) | Purity (%) | Distillation yield (%) | Purity (%) | Recovery Rate (%) |
| Process of this invention: | | | | | | | | |
| silica-alumina, zinc chloride, hydrochloric acid | n-hexane | 68 | 4 | 99.8 | 95.8 | 78.0 | 97.3 | 75.9 |
| silica-alumina, zinc chloride, hydrochloric acid | toluene | 110 | 4 | 99.7 | 95.6 | 78.5 | 97.1 | 76.2 |
| silica gel, zinc chloride, hydrochloric acid | toluene | 110 | 4 | 99.5 | 96.0 | 77.1 | 97.5 | 75.2 |
| silica-alumina, zinc chloride, sulfuric acid | toluene | 110 | 4 | 99.2 | 95.1 | 77.4 | 96.5 | 74.7 |
| silica-alumina, zinc chloride, phosphoric acid | n-hexane | 68 | 4 | 99.4 | 95.0 | 76.2 | 96.4 | 73.5 |
| Prior art process: | | | | | | | | |
| silica-alumina | toluene | 110 | 3 | 94.7 | 49.2 | 75.4 | 56.2 | 42.4 |
| silica-alumina | n-hexane | 68 | 5 | 92.6 | 40.3 | 78.0 | 48.9 | 38.1 |
| silica gel | toluene | 110 | 4 | 94.2 | 40.2 | 76.1 | 45.2 | 34.4 |
| silica-alumina, zinc chloride | toluene | 110 | 4 | 98.2 | 92.5 | 76.2 | 94.0 | 71.6 |

Table 1-continued

| | Reaction Condition | | | dl-α-tocopherol | | dl-α-tocopherol acetate | | |
|---|---|---|---|---|---|---|---|---|
| Catalyst used | Reaction solvent | Reaction temperature | Reaction time (hr) | Yield (%) | Purity (%) | Distillation yield (%) | Purity (%) | Recovery Rate (%) |
| zinc chloride, hydrochloric acid | toluene | 110 | 4 | 99.7 | 93.0 | 76.8 | 95.0 | 73.0 |

The process of this invention will be explained concretely in the following Examples but the present invention will not be limited to these Examples.

Example 1

13.5 g of trimethyl hydroquinone are dissolved in 100 ml of toluene, and 13.5 g of silica-alumina, 6.0 g of zinc chloride and 0.5 g of concentrated hydrochloric acid (35% hydrochloric acid) are added thereto under nitrogen flow. The reaction system is warmed to 85° C. and then 25.0 g of isophytol are added dropwise over about 20 minutes. After completion of the addition, stirring is continued for about 4 hours at the same temperature and then the reaction system is allowed to cool. Then, 100 ml of toluene are added to the reaction mixture and the insoluble material is filtered off. The filtrate is washed in succession with 3% caustic soda, 1% sodium hydrosulfite, water and saturated aqueous salt solution and dehydrated with anhydrous magnesium sulfate. The solvent is then distilled off under reduced pressure to give 36.2 g of dl-α-tocopherol (yield 99.8%). 25.0 g of dl-α-tocopherol thus obtained are dissolved in 50 ml of acetic anhydride and 12.5 g of sodium acetate and 1.25 g of metallic zinc powder are added thereto. The reaction mixture is acetylated by stirring at 95°-100° C. for about 3.5 hours and then extracted with 200 ml of n-hexane. The extract is washed in succession with 1% caustic soda, water and saturated aqueous salt solution and dried over magnesium sulfate. Thereafter, n-hexane is distilled off under reduced pressure to give 26.2 g of crude dl-α-tocopherol acetate. The crude dl-α-tocopherol acetate thus obtained is subjected to vacuum distillation to give 20.5 g of the main fraction of 165°-175° C./8×10$^{-3}$ mmHg. The purity of this product is 97.3% and the distillation yield is 78.0%.

Example 2

13.5 g of trimethyl hydroquinone are dispersed in 100 ml of carbon tetrachloride and 13.5 g of silica gel, 6.0 g of zinc chloride and 0.5 g of concentrated hydrochloric acid (35% hydrochloric acid) are added thereto under nitrogen flow. The reaction system is warmed to 78° C. and then 25.0 g of isophytol are added dropwise over about 20 minutes. After completion of the addition, stirring is continued for about 4 hours and then the reaction system is allowed to cool.

To the reaction mixture are added 100 ml of carbon tetrachloride. The insoluble material is filtered off and the filtrate is washed in succession with 3% caustic soda/1% hydrosulfite soda mixture, water and saturated aqueous salt solution and dehydrated with anhydrous magnesium sulfate. Then, the solvent is distilled off under reduced pressure to give 36.0 g of dl-α-tocopherol (yield 99.1%, purity 95.3%).

Then, 25.0 g of dl-α-tocopherol thus obtained are dissolved in 50 ml of acetic anhydride and 12.5 g of sodium acetate and 1.25 g of metallic zinc powder are added thereto. The reaction mixture is then acetylated by stirring at 95°-100° C. for about 3.5 hours and thereafter the end product is extracted with 200 ml of n-hexane. The extract is washed in succession with 1% caustic soda, water and saturated aqueous salt solution and dried over magnesium sulfate. Then, n-hexane is distilled off under reduced pressure to give 25.8 g of crude dl-α-tocopherol acetate.

The resulting crude dl-α-tocopherol acetate is then subjected to vacuum distillation to give 19.6 g of the main distillation fraction of 165°-175° C./8×10$^{-3}$ mmHg (distillation yield 76.0%, purity 96.8%).

What we claim is:

1. A process for the preparation of dl-α-tocopherol of high purity, characterized by condensing trimethyl hydroquinone and a phytol in the presence of (a) silica-alumina, zinc chloride and an acid selected from the group consisting of sulfuric acid, phosphoric acid, p-toluenesulfonic acid and hydrochloric acid, or (b) silica gel, zinc chloride and an acid selected from the group consisting of sulfuric acid, phosphoric acid, p-toluenesulfonic acid and hydrochloric acid.

* * * * *